United States Patent
Spagnol et al.

(12)

(10) Patent No.: US 6,194,616 B1
(45) Date of Patent: Feb. 27, 2001

(54) ACYLATION METHOD FOR AN AROMATIC COMPOUND

(75) Inventors: Michel Spagnol; Laurent Gilbert, both of Lyons; Henri Guillot, Sainte Foy les Lyon; Philippe-Jean Tirel, Comunay, all of (FR)

(73) Assignee: Rhodia Chimie, Courebevoie Cedex (FR)

( * ) Notice: Subject to any disclaimer, the term of this patent is extended or adjusted under 35 U.S.C. 154(b) by 0 days.

(21) Appl. No.: 09/202,666

(22) PCT Filed: Jun. 13, 1997

(86) PCT No.: PCT/FR97/01066

§ 371 Date: Apr. 6, 1999

§ 102(e) Date: Apr. 6, 1999

(87) PCT Pub. No.: WO97/48665

PCT Pub. Date: Dec. 24, 1997

(30) Foreign Application Priority Data

Jun. 20, 1996 (FR) .................................................. 96-07691

(51) Int. Cl.$^7$ .................................................. C07C 45/45
(52) U.S. Cl. ...................... 568/322; 568/319; 568/332; 568/335
(58) Field of Search .................... 568/319, 332, 568/322, 323, 373, 335; 560/52

(56) References Cited

U.S. PATENT DOCUMENTS 4,835,319 * 5/1989 Corbin et al. ........................ 568/322
4,960,943 * 10/1990 Botta et al. .......................... 568/319
5,164,527 * 11/1992 Newton ................................. 560/52
5,227,529 * 7/1993 Neuber et al. ....................... 568/319

FOREIGN PATENT DOCUMENTS

| 0 316 133 | 5/1989 | (EP) . |
| 0 334 096 | 9/1989 | (EP) . |
| 0 455 332 | 11/1991 | (EP) . |
| 0 459 495 | 12/1991 | (EP) . |
| 0 701 987 | 3/1996 | (EP) . |
| 2 667 063 | 3/1992 | (FR) . |
| 96 21637 | 7/1996 | (WO) . |
| 96 35656 | 11/1996 | (WO) . |

* cited by examiner

*Primary Examiner*—Sreeni Padmanabhan
(74) *Attorney, Agent, or Firm*—Burns, Doane, Swecker & Mathis, L.L.P.

(57) ABSTRACT

The present invention concerns a process for acylation of an aromatic compound.

The acylation process of the invention consists of reacting the aromatic compound with an acylation agent in the presence of a zeolitic catalyst, and is characterized in that it consists of:

mixing the aromatic compound and the acylation compound in any manner;

passing said mixture over a catalytic bed comprising at least one zeolite;

recirculating the reaction mixture from the catalytic bed over the catalytic bed for a number of times which is sufficient to obtain the desired degree of conversion of the substrate.

35 Claims, 1 Drawing Sheet

FIG. 1

ACYLATION METHOD FOR AN AROMATIC COMPOUND

This is the U.S. National Stage Application of PCT/FR97/01066 filed Jun. 13, 1997.

The present invention concerns a process for the acylation of an aromatic compound, in particular an aromatic ether or thioether.

In its preferred variation, the invention concerns a process for the acylation of an aromatic ether or thioether by carboxylic acid anhydrides, preferably acetic anhydride.

More particularly, the invention is applicable to the preparation of alkoxy- or alkylthio-aromatic alkylketones.

Conventional processes for the acylation of aromatic compounds, in particular the ethers of phenols, use a carboxylic acid or one of its derivatives such as the acid halide, ester or anhydride as the acylation reactant.

The reaction is generally carried out in the presence of a Lewis acid type catalyst (for example $AlCl_3$) or a Brönsted acid type catalyst ($H_2SO_4$, HF, etc . . . ).

For about ten years, zeolites have been used as acylation catalysts.

Thus European patent EP-A-0 279 322 describes the vapour phase reaction of an aromatic compound (veratrole) with a carboxylic acid derivative in the presence of a zeolite in its H form such as mordenite, faujasite and ZSM-5.

U.S. Pat. No. 4,960,943 describes an acylation process, particularly for anisole, in the presence of zeolites which have a pore size of at least 5 Angstroms and which have the following formula: $M_{m/z}[mMe^1O_2.nMe^2O_2],qH_2O]$ where M is an exchangeable cation, z is the valency of the cation and $Me^1$ and $Me^2$ represent the elements of the anionic skeleton, n/m is a number from 1–3000, preferably 1–2000, and q represents the adsorbed water.

Prins et al. have described the acetylation of anisole using acetic anhydride [$9^{th}$ International Zeolite Congress-Montreal Congress (1992)], in the presence of zeolites such as β zeolite or US-Y zeolite. It should be noted that β zeolites can produce more interesting results as regards both the degree of conversion and the reaction yield.

However, the catalyst performances described are not satisfactory. The use of such a catalyst on an industrial scale is problematic since the productivity of the catalyst is unsatisfactory and would thus necessitate the use of a very large reactor.

The aim of the present invention is to provide a process which can overcome the above disadvantages.

It has now been discovered, and this constitutes the aim of the present invention, a process for the acylation of an aromatic compound, by reacting said compound with an acylation agent in the presence of a zeolitic catalyst, characterized in that it consists of:
mixing the aromatic compound and the acylation compound in any manner;
passing said mixture over a catalytic bed comprising at least one zeolite;
recirculating the reaction mixture from the catalytic bed over the catalytic bed for a number of times which is sufficient to obtain the desired degree of conversion of the substrate.

The process of the invention thus uses an aromatic compound and an acylation agent.

In the following disclosure of the present invention, the term "aromatic compound" encompasses the conventional concept of aromaticity as defined in the literature, in particular by Jerry MARCH, "Advanced Organic Chemistry", $4^{th}$ edition, John Wiley and Sons, 1992, p40 ff.

The term "by an aromatic ether or thioether" means an aromatic compound in which one hydrogen atom which is directly bonded to the aromatic ring has been replaced by an ether or thioether group respectively.

More precisely, the present invention provides a process for acylation of an aromatic compound with general formula (I):

where:
A represents the residue of a cycle forming all or part of a carbocyclic or heterocyclic, aromatic, monocyclic or polycyclic system; said cyclic residue may carry a radical R which represents a hydrogen atom or one or more substituents, which may be identical or different;
n represents the number of substituents in the cycle.

The invention is particularly applicable to aromatic compounds with formula (I) in which A is the residue of a cyclic compound which preferably contains at least 4 atoms in the cycle, preferably 5 or 6, which may be substituted, and which represents at least one of the following cycles:
an aromatic, monocyclic or polycyclic carbocycle;
an aromatic, monocyclic or polycyclic heterocycle comprising at least one of heteroatoms O, N or S.

In more detail, without in any way limiting the scope of the invention, residue A which may optionally be substituted represents the residue:
1° of an aromatic, monocyclic or polycyclic carbocyclic compound.
  The term "polycyclic carbocyclic compound" means:
  a compound constituted by at least 2 aromatic carbocycles and forming ortho- or ortho- and peri-condensed systems between them;
  a compound constituted by at least 2 carbocycles, only one of them being aromatic and forming ortho- or ortho- and peri-condensed systems between them;
2° of an aromatic, monocyclic or polycyclic heterocyclic compound.
  The term "polycyclic heterocyclic compound" defines:
  a compound constituted by at least 2 heterocycles containing at least one heteroatom in each cycle, at least one of the two cycles being aromatic and forming ortho- or ortho- and peri-condensed systems between them;
  a compound constituted by at least one hydrocarbon cycle and at least one heterocycle, at least one of the cycles being aromatic and forming ortho- or ortho-and peri-condensed systems between them;
3° of a compound constituted by linked cycles as defined in paragraphs 1 and/or 2 linked together by:
  a valence bond;
  an alkylene or alkylidene radical containing 1 to 4 carbon atoms, preferably a methylene radical or an isopropylidene radical;
  one of the following groups:

in these formulae, $R_0$ represents a hydrogen atom or an alkyl radical containing 1 to 4 carbon atoms, or a cyclohexyl or phenyl radical.

More particularly, residue A which may optionally be substituted represents the residue:

- of an aromatic carbocyclic monocyclic compound such as benzene, toluene, isobutylbenzene, anisole, thioanisole, phenetole or veratrole, guaiacol or guetol;
- of an aromatic condensed polycyclic compound, such as naphthalene or 2-methoxynaphthalene;
- of an aromatic carbocyclic, non condensed polycyclic compound such as phenoxybenzene;
- of a partially aromatic carbocyclic condensed polycyclic compound such as tetrahydronaphthalene or 1,2-methylenedioxybenzene;
- of a partially aromatic carbocyclic non condensed polycyclic compound such as cyclohexylbenzene;
- of an aromatic heterocyclic monocyclic compound such as pyridine, furan or thiophene;
- of a partially heterocyclic aromatic condensed polycyclic compound such as quinoline, indole or benzofuran;
- of a partially heterocyclic aromatic, non condensed polycyclic compound such as phenylpyridines, or naphthylpyridines;
- of a partially heterocyclic, partially aromatic condensed polycyclic compound such as tetrahydroquinoline;
- of a partially heterocyclic, partially aromatic, non condensed polycyclic compound such as cyclohexylpyridine.

In the process of the invention, an aromatic compound with formula (I) is preferably used in which A represents an aromatic nucleus, preferably a benzenic or naphthalene nucleus.

The aromatic compound with formula (I) can carry one or more substituents.

The number of substituents present in the cycle depend on the carbon condensation of the cycle and the presence or otherwise of unsaturations in the cycle.

The maximum number of substituents which can be carried by a cycle can readily be determined by the skilled person.

In the present description, the term "several" generally means less than 4 substituents on one aromatic nucleus.

Examples of substituents are given below but these are not limiting.

Radicals R, which may be identical or different, preferably represent one of the following groups:

- a hydrogen atom;
- a linear or branched alkyl radical containing 1 to 6 carbon atoms, preferably 1 to 4 carbon atoms, such as methyl, ethyl, propyl, isopropyl, butyl, isobutyl, sec-butyl, tert-butyl;
- a linear or branched alkenyl radical containing 2 to 6 carbon atoms, preferably 2 to 4 carbon atoms, such as vinyl, allyl;
- a linear or branched alkoxy radical containing 1 to 6 carbon atoms, preferably 1 to 4 carbon atoms, such as methoxy, ethoxy, propoxy, isopropoxy, or butoxy radicals, or an alkenyloxy radical, preferably an allyloxy or a phenoxy radical;
- a cyclohexyl, phenyl or benzyl radical;
- an acyl group containing 2 to 6 carbon atoms;
- a radical with formula:
  —$R_1$—OH
  —$R_1$—$COOR_2$
  —$R_1$—CHO
  —$R_1$—$NO_2$
  —$R_1$—CN
  —$R_1$—$N(R_2)_2$
  —$R_1$—CO—$N(R_2)_2$
  —$R_1$—X
  —$R_1$—$CF_3$ in said formulae, $R_1$ represents a valence bond or a divalent, linear or branched, saturated or unsaturated hydrocarbon radical containing 1 to 6 carbon atoms, such as methylene, ethylene, propylene, isopropylene, or isopropylidene; radicals $R_2$, which may be identical or different, represent a hydrogen atom or a linear or branched alkyl radical containing 1 to 6 carbon atoms; X represents a halogen atom, preferably a chlorine, bromine or fluorine atom;

two radicals R placed on two neighbouring carbon atoms may together form with the carbon atoms they carry a cycle containing 5 to 7 atoms, optionally comprising a further heteroatom.

When n is greater than or equal to 2, two radicals R and the 2 successive atoms of the aromatic cycle can be bonded together by an alkylene, alkenylene or alkenylidene radical containing 2 to 4 carbon atoms to form a saturated, unsaturated or aromatic heterocycle containing 5 to 7 carbon atoms. One or more carbon atoms can be replaced by a further heteroatom, preferably oxygen or sulphur. Thus radicals R can represent a methylenedioxy or ethylenedioxy radical or a methylenedithio or ethylenedithio radical.

The present invention is particularly applicable to aromatic compounds with formula (I) in which radicals R represent an electron-donating group.

In the present description, the term "electron-donating group" means a group as defined by H. C. BROWN in the book by Jerry MARCH, "Advanced Organic Chemistry", Chapter 9, pages 243 and 244 (1985).

The aromatic compounds which are preferably used have formula (Ia):

(Ia)

where:

A represents the residue of a cycle forming all or part of an aromatic, monocyclic or polycyclic, carbocyclic or heterocyclic system: said cyclic residue can carry a radical R representing a hydrogen atom or one or more electron-donating substituents, which may be identical or different;

n represents the number of substituents in the cycle.

Examples of preferred electron-donating groups R are:

- a linear or branched alkyl radical containing 1 to 6 carbon atoms, preferably 1 to 4 carbon atoms, such as methyl, ethyl, propyl, isopropyl, butyl, isobutyl, sec-butyl, tert-butyl;
- a linear or branched alkenyl radical containing 2 to 6 carbon atoms, preferably 2 to 4 carbon atoms, such as vinyl, allyl;
- a cyclohexyl, phenyl or benzyl radical;
- a linear or branched alkoxy radical containing 1 to 6 carbon atoms, preferably 1 to 4 carbon atoms, such as methoxy, ethoxy, propoxy, isopropoxy, or butoxy radicals, or an alkenyloxy radical, preferably an allyloxy or a phenoxy radical;

a radical with formula:
—$R_1$—OH
—$R_1$—$N(R_2)_2$ in said formulae, $R_1$ represents a valence bond or a divalent, linear or branched, saturated or unsaturated hydrocarbon radical containing 1 to 6 carbon atoms such as methylene, ethylene, propylene, isopropylene, or isopropylidene; radicals $R_2$, which may be identical or different, represent a hydrogen atom or a linear or branched alkyl radical containing 1 to 6 carbon atoms;

two radicals R may be bonded together to form alkylenedioxy or alkylenedithio radicals, preferably a methylenedioxy, ethylenedioxy, methylenedithio or ethylenedithio radical.

In formula (Ia), n is a number which is less than or equal to 4, preferably 1 or 2.

As mentioned above, the process of the invention is particularly suitable for the acylation of aromatic ethers and thioethers.

The preferred formula for said compounds is:

(I')

where:

Y represents an oxygen atom or a sulphur atom;

A represents the residue of a cycle forming all or a portion of an aromatic, monocyclic or polycyclic carbocyclic system comprising at least one group YR': said cyclic residue may carry one or more substituents;

R represents one or more substituents, which may be identical or different;

R' represents a hydrocarbon radical containing 1 to 24 carbon atoms, which can be a linear or branched, saturated or unsaturated acyclic aliphatic radical; a saturated, unsaturated or aromatic, monocyclic or polycyclic cycloaliphatic radical; or a saturated or unsaturated, linear or branched aliphatic radical carrying a cyclic substituent;

R' and R can form a cycle which optionally comprises a further heteroatom;

n is a number which is less than or equal to 4.

For simplification in the present text, the term "alkoxy or thioether" respectively designates R'—O— or R'—S— type groups where R' has the meaning given above. R' can thus represent both a saturated, unsaturated or aromatic, acyclic or cycloaliphatic aliphatic radical and a saturated or unsaturated aliphatic radical carrying a cyclic substituent.

The aromatic ether or thioether used in the process of the invention has formula (I') where R' represents a linear or branched, saturated or unsaturated, acyclic aliphatic radical.

More preferably, R' represents a linear or branched alkyl radical containing 1 to 12 carbon atoms, preferably 1 to 6 carbon atoms: the hydrocarbon chain can optionally be interrupted by a heteroatom (for example oxygen), by a functional group (for example —CO—) and/or may carry substituents (for example, one or more halogen atoms).

The linear or branched, saturated or unsaturated, acyclic aliphatic radical can optionally carry a cyclic substituent.

The term "cycle" preferably means a saturated, unsaturated or aromatic carbocyclic cycle, preferably cycloaliphatic or aromatic, particularly cycloaliphatic containing 6 carbon atoms in the cycle, or benzenic.

The acyclic aliphatic radical can be connected to the cycle by a valence bond, a heteroatom or a functional group and examples are given below.

The cycle can optionally be substituted and examples of cyclic substituents are, among others, substituents such as R, the meaning of which has been defined for formula (I').

R' can also represent a carbocyclic radical which is saturated or which comprises 1 or 2 unsaturations in the cycle, generally containing 3 to 8 carbon atoms, preferably 6 carbon atoms in the cycle; said cycle can be substituted by substituents such as R.

R' can also represent an aromatic carbocyclic radical, preferably monocyclic generally containing at least 4 carbon atoms, preferably 6 carbon atoms in the cycle; said cycle can be substituted by substituents such as R In general formula (I') for aromatic ethers or thioethers, residue A can represent the residue of an aromatic monocyclic carbocyclic compound containing at least 4 carbon atoms, preferably 6 carbon atoms, or the residue of a polycyclic carbocyclic compound which can be constituted by at least two aromatic carbocycles and form between them ortho- or ortho- and peri-condensed systems or by at least 2 carbocycles, at least one of them being aromatic and forming between them ortho- or ortho- and peri-condensed systems. A naphthalenic residue can be cited in particular.

Residue A can carry one or more substituents on the aromatic nucleus.

Reference can be made to the examples of substituents given for formula (I) but this list is not limiting. Any substituent can be present on the cycle provided that it does not interfere with the desired product.

Since residue A can, among others, carry several alkoxy groups, it is possible to use the process of the invention to acylate polyalkoxylated compounds.

In formula (I'), R more preferably represents one of the following atoms or groups:

a linear or branched alkyl radical containing 1 to 6 carbon atoms, preferably 1 to 4 carbon atoms, such as methyl, ethyl, propyl, isopropyl, butyl, isobutyl, sec-butyl or tert-butyl;

a linear or branched alkoxy radical containing 1 to 6 carbon atoms, preferably 1 to 4 carbon atoms, such as methoxy, ethoxy, propoxy, isopropoxy, butoxy, isobutoxy, sec-butoxy, or tert-butoxy;

a halogen atom, preferably a fluorine, chlorine or bromine atom, or a trifluoromethyl radical.

The process of the invention is of particular application to aromatic ethers or thioethers with formula (I'a):

(I'a)

where:

n is a number which is less than or equal to 4, preferably 0 or 1;

Y represents an oxygen atom or a sulphur atom;

radical R' represents a linear or branched alkyl radical containing 1 to 6 carbon atoms, preferably 1 to 4 carbon atoms, such as methyl, ethyl, propyl, isopropyl, butyl, isobutyl, sec-butyl, tert-butyl or a phenyl radical;

radical(s) R, which may be identical or different, represent one of the following atoms or groups:

a hydrogen atom;

a linear or branched alkyl radical containing 1 to 6 carbon atoms, preferably 1 to 4 carbon atoms, such as methyl, ethyl, propyl, isopropyl, butyl, isobutyl, sec-butyl, or tert-butyl;

a linear or branched alkenyl radical containing 2 to 6 carbon atoms, preferably 2 to 4 carbon atoms, such as vinyl, allyl;

a linear or branched alkoxy radical containing 1 to 6 carbon atoms, preferably 1 to 4 carbon atoms, such as methoxy, ethoxy, propoxy, isopropoxy, or butoxy radicals, or an alkenyloxy radical, preferably an allyloxy or a phenoxy radical;

a cyclohexyl, phenyl or benzyl radical;

a an acyl group containing 2 to 6 carbon atoms;

a radical with formula:

in said formulae, $R_1$ represents a valence bond or a divalent, linear or branched, saturated or unsaturated hydrocarbon radical containing 1 to 6 carbon atoms such as methylene, ethylene, propylene, isopropylene, or isopropylidene; radicals $R_2$, which may be identical or different, represent a hydrogen atom or a linear or branched alkyl radical containing 1 to 6 carbon atoms; X represents a halogen atom, preferably a chlorine, bromine or fluorine atom;

radicals R and R' placed on two neighbouring carbon atoms may together form with the carbon atoms they carry a cycle containing 5 to 7 atoms, optionally comprising a further heteroatom.

When n is greater than or equal to 1, radicals R' and R and the 2 successive atoms of the benzenic cycle can be bonded together to form an alkylene, alkenylene or alkenylidene radical containing 2 to 4 carbon atoms to form a saturated, unsaturated or aromatic heterocycle containing 5 to 7 atoms. One or more carbon atoms can be replaced by a further heteroatom, preferably oxygen or sulphur. Thus radicals OR' and R can represent a methylenedioxy or ethylenedioxy radical and radicals SR' and R can represent a methylenedithio or ethylenedithio radical.

In formula (I'a), R' preferably represents a linear or branched alkyl radical containing 1 to 6 carbon atoms, preferably a methyl or ethyl radical or a phenyl radical.

The benzenic nucleus carries one or more substituents R which may be identical or different. R preferably represents a linear or branched alkyl radical containing 1 to 6 carbon atoms, preferably a methyl or ethyl radical; or a linear or branched alkoxy radical containing 1 to 4 carbon atoms, preferably a methoxy or ethoxy radical.

The process of the invention is particularly applicable to aromatic ethers and thioethers with formula (I') or (I'a) where:

n equals 0 or 1;

R' represents a linear or branched alkyl radical containing 1 to 6 carbon atoms or a phenyl radical, preferably a methyl or ethyl radical;

R represents a linear or branched alkyl radical containing 1 to 6 carbon atoms, preferably a methyl or ethyl radical; or a linear or branched alkoxy radical containing 1 to 4 carbon atoms, preferably a methoxy or ethoxy radical;

radicals YR' and R form a methylenedioxy, ethylenedioxy, methylenedithio or ethylenedithio radical.

Particular illustrations of compounds with formula (I) or (I') are:

aromatic compounds such as benzene, toluene, fluorobenzene, chlorotoluenes, fluorotoluenes, trifluoromethoxybenzene, trichloromethoxybenzene, or trifluoromethylthiobenzene;

aromatic amine-containing compounds such as aniline;

phenolic compounds such as phenol, o-cresol, guaiacol, guetol, α-naphthol, or β-naphthol;

monoethers such as anisole, ethoxybenzene (phenetole), propoxybenzene, isopropoxybenzene, butoxybenzene, isobutoxybenzene, 1-methoxynaphthalene, 2-methoxynaphthalene, or 2-ethoxynaphthalene; substituted monoethers such as 2-chloroanisole, 3-chloroanisole, 2-bromoanisole, 3-bromoanisole, 2-methylanisole, 3-methylanisole, 2-ethylanisole, 3-ethylanisole, 2-isopropylanisole, 3-isopropylanisole, 2-propylanisole, 3-propylanisole, 2-allylanisole, 2-butylanisole, 3-butylanisole, 2-benzylanisole, 2-cyclohexylanisole, 1-bromo-2-ethoxybenzene, 1-bromo-3-ethoxybenzene, 1-chloro-2-ethoxybenzene, 1-chloro-3-ethoxybenzene, 1-ethoxy-2-ethylbenzene, 1-ethoxy-3-ethylbenzene, 1-methoxy-2-allyloxybenzene, 2,3dimethylanisole, or 2,5-dimethylanisole;

diethers such as veratrole, 1,3-dimethoxybenzene, 1,4dimethoxybenzene, 1,2-diethoxybenzene, 1,3-diethoxybenzene, 1,2-dipropoxybenzene, 1,3-dipropoxybenzene, 1,2-methylenedioxybenzene, or 1,2-ethylenedioxybenzene;

triethers such as 1,2,3-trimethoxybenzene, 1,3,5-trimethoxybenzene, or 1,3,5-triethoxybenzene;

thioethers such as thioanisole, o-thiocresol, m-thiocresol, p-thiocresol, 2-thioethylnaphthalene, S-phenylthioacetate, 3-(methylmercapto)aniline, or phenylthiopropionate.

Benzene, toluene, isobutylbenzene, anisole, phenetole, veratrole, 1,2-methylenedioxybenzene, 2-methoxynaphthalene and thioanisole are compounds to which the process of the invention is particularly applicable.

Regarding the acylation reactant, carboxylic acids and their halide or anhydride derivatives are used, preferably anhydrides.

More particularly, the acylation reactant has formula (II):

(II)

where:

$R_3$ represents:

a linear or branched, saturated or unsaturated aliphatic radical containing 1 to 24 carbon atoms; a monocyclic or polycyclic, saturated, unsaturated or aromatic cycloaliphatic radical containing 3 to 8 carbon atoms; or a linear or branched, saturated or unsaturated aliphatic radical carrying a cyclic substituent;

X' represents:

a halogen atom, preferably a chlorine or bromine atom;

a hydroxyl group;

a —O—CO—$R_4$ radical, where $R_4$, which may be identical to or different from $R_3$, has the same meaning as $R_3$: $R_3$ and $R_4$ may together form a divalent linear or branched, saturated or unsaturated aliphatic radical containing at least 2 carbon atoms.

Reference should be made to the above description for the meaning of the term "cyclic substituent".

More preferably, $R_3$ represents a linear or branched alkyl radical containing 1 to 12 carbon atoms, preferably 1 to 6 carbon atoms: the hydrocarbon chain can optionally be interrupted by a heteroatom (for example oxygen), by a functional group (for example —CO—) and/or may carry a substituent (for example a halogen or a $CF_3$ group).

$R_3$ preferably represents an alkyl radical containing 1 to 4 carbon atoms, such as methyl, ethyl, propyl, isopropyl, butyl, isobutyl, sec-butyl, or tert-butyl.

$R_3$ also represents an alkenyl radical containing 2 to 10 carbon atoms, such as vinyl, propen-yl, buten-yl, penten-yl, hexen-yl, octen-yl, or decen-yl.

Preferably, radical $R_3$ also represents a phenyl radical which can optionally be substituted. Any substituent can be present on the cycle provided that it does not interfere with the desired product.

Particular examples of substituents are:
a linear or branched alkyl radical containing 1 to 6 carbon atoms, preferably 1 to 4 carbon atoms, such as methyl, ethyl, propyl, isopropyl, butyl, isobutyl, sec-butyl, or tert-butyl;
a linear or branched alkoxy radical containing 1 to 6 carbon atoms, preferably 1 to 4 carbon atoms such as methoxy, ethoxy, propoxy, isopropoxy, butoxy, isobutoxy, sec-butoxy, or tert-butoxy;
a hydroxyl group;
a halogen atom, preferably a fluorine, chlorine or bromine atom.

Preferred acylation agents are acid anhydrides. More particularly, they have formula (II) where $R_3$ and $R_4$ are identical and represent an alkyl radical containing 1 to 4 carbon atoms or a phenyl radical.

When the acylation agent is an acid halide, it preferably has formula (II) where X' represents a chlorine atom and $R_3$ represents a methyl, ethyl or phenyl radical.

Particular illustrative examples of acylation agents with formula (II) are:
acetic anhydride;
propanoic anhydride
butyric anhydride;
isobutyric anhydride;
trifluoroacetic anhydride;
benzoic anhydride;
monochloroacetyl anhydride;
dichloroacetyl anhydride;
acetyl chloride;
monochloroacetyl chloride;
dichloroacetyl chloride;
propanoyl chloride;
isobutanoyl chloride;
pivaloyl chloride;
stearoyl chloride;;
crotonyl chloride;
benzoyl chloride;
chlorobenzoyl chlorides;
p-nitrobenzoyl chloride;
methoxybenzoyl chlorides;
naphthoyl chlorides;
acetic acid;
benzoic acid.

Preferred acylation agents are acetic, propanoic, benzoic, monochloroacetyl, and dichloroacetyl anhydride, also benzoyl chloride.

In accordance with the invention, the acylation reaction is carried out in the presence of a zeolitic catalyst.

The term "zeolite" means a crystallised tectosilicate of natural or synthetic origin, the crystals of which result from the three-dimensional assembly of $SiO_4$ and $TO_4$ tetrahedra: T represents a trivalent element such as aluminium, gallium, boron, or iron, preferably aluminium.

Aluminosilicate type zeolites are the most common.

The crystalline framework of a zeolite has a system of cavities linked together by channels, termed pores, of a well defined diameter.

Zeolites can have a one-dimensional, two-dimensional or three-dimensional network of channels.

The process of the invention uses a natural or a synthetic zeolite.

Examples of natural zeolites which can be used are: chabazite, clinoptilolite, erionite, phillipsite, and offretite.

Synthetic zeolites are also suitable for use in the process of the invention.

Examples of zeolites with a one-dimensional network are ZSM-4 zeolite, L zeolite, ZSM-12 zeolite, ZSM-22 zeolite, ZSM-23 zeolite, and ZSM-48 zeolite.

Preferred examples of zeolites with a two-dimensional network are β zeolite, mordenite, and ferrierite.

Particular examples of zeolites with a three-dimensional network are Y zeolite, X zeolite, ZSM-5 zeolite, ZSM-11 zeolite, and offretite.

Preferably, synthetic zeolites are used, more particularly zeolites in the following forms:
mazzite with a Si/Al molar ratio of 3.4;
L zeolite with a Si/Al molar ratio of 1.5 to 3.5;
mordenite with a Si/Al molar ratio of 5 to 15;
ferrierite with a Si/Al molar ratio of 3 to 10;
offretite with a Si/Al molar ratio of 4 to 8.5;
β zeolites with a Si/Al molar ratio of more than 8, preferably in the range 10 to 100, more preferably between 12 and 50;
Y zeolites, in particular the zeolites obtained after dealumination (for example hydrotreatment, washing using hydrochloric acid or treatment with $SiCl_4$), more particularly US-Y zeolites with a Si/Al molar ratio of more than 3, preferably in the range 6 to 60;
X zeolite of faujasite type with a Si/Al molar ratio of 0.7 to 1.5;
ZSM-5 zeolite or aluminium silicalite with a Si/Al molar ratio of 10 to 500;
ZSM-11 with a Si/Al molar ratio of 5 to 30;
mesoporous MCM type zeolite, more particularly MCM-22 and MCM-41 with a Si/Al molar ratio which is in the range 10 to 100, preferably in the range 15 to 40.

Of all these zeolites, β and Y zeolites are preferably used in the process of the invention.

The zeolites used in the process of the invention are known products described in the literature [see "Atlas of Zeolite Structure Types" by W. M. Meier and D. H. Olson, published by the Structure Commission of the International Zeolite Association (1978)].

Commercially available zeolites can be used, or they can be synthesised using processes described in the literature.

Reference can be made to the Atlas mentioned above, more particularly for the preparation of:
L zeolite from the publication by R. M. Barrer et al., Z. Kristallogr., 128, pp. 352 (1969);
ZSM-12 zeolite from U.S. Pat. No. 3,832,449 and the article by LaPierre et al., Zeolites 5, pp 346 (1985);

ZSM-22, in the publication by G. T. Kokotailo et al., Zeolites 5, pp. 349 (1985);
of ZSM-23 zeolite, from U.S. Pat. No. 4,076,842 and the article by A. C. Rohrman et al., Zeolites 5, pp. 352 (1985);
ZSM-48 zeolite, from the work by J. L. Schlenker et al., Zeolites 5, pp. 355 (1985)
β zeolite, from U.S. Pat. No. 3,308,069 and the article by P. Caullet et al., Zeolites 12, 240 (1992);
mordenite, from the work by Itabashi et al., Zeolites 6, pp. 30 (1986);
X and Y zeolites respectively from U.S. Pat. No. 2,882,244 and U.S. Pat. No. 3,130,007;
ZSM5 zeolite, from U.S. Pat. No. 3,702,886 and the article by V. P. Shiralkar et al., Zeolites 9, pp. 363 (1989);
ZSM-11 zeolite, from the work by I. D. Harrison et al., Zeolites 7, p. 21 (1987);
mesoporous MCM type zeolite, from the article by Beck et al., J. Am. Chem. Soc., 114, pp. 10834–43 (1992).

The zeolite constitutes the catalytic phase. It can be used alone or mixed with an inorganic matrix. In the description, the term "catalyst" refers to the catalyst which is all zeolite or to a mixture with a matrix prepared using the techniques known to the skilled person.

To this end, the matrix can be selected from oxides of metals such as aluminium, silicon and/or zirconium oxides, or from clays, more particularly kaolin, talc or montmorillonite.

The amount of active phase in the catalyst can be 5% to 100% of the weight of the catalyst.

The catalysts can be in different forms in the process of the invention: powder, formed products such as granulates (for example extrudates or spherules), or pellets, obtained by extrusion, moulding, compacting or any other type of known process. In practice, on an industrial scale, these are the forms of granulates or spherules which have the most advantages as regards efficacity and ease of use.

In accordance with the invention, the acylation reaction is carried out using a process for recirculation of the reaction mixture over a fixed bed of catalyst.

The process is begun by forming the mixture of the aromatic compound and the acylation agent in any manner.

Thus, the aromatic compound and the acylation agent can be mixed in a mixing zone and the mixture obtained can then be sent over the catalytic bed.

In a further variation, one of the reactants (aromatic compound or acylation agent) can be introduced and sent over the catalytic bed and then the other reactant can be added all at once or gradually when the desired reaction temperature is reached. In this way, and preferably, the aromatic compound is introduced then the acylation agent is gradually added.

The invention encompasses introducing the mixture of reactants then adding one of two other reactants at the desired temperature so as to obtain the desired aromatic compound/acylation agent ratio.

The final ratio between the number of moles of aromatic compound and the number of moles of acylation agent can vary widely. Thus the ratio can be from 0.1 to 20, preferably between 0.5 and 10.

In a preferred implementation of the invention, in order to increase the yield and maintain the activity of the catalyst, an excess of aromatic compound is used. Thus an aromatic compound/acylation agent molar ratio is selected which is at least 1, preferably in the range 1 to 20, more preferably in the range 1 to 10.

One of the reactants is generally used as the reaction solvent, but the use of an organic solvent, the nature of which is determined by the skilled person, is not excluded.

In a preferred implementation of the process of the invention, the temperature of the mixture is brought to the temperature at which the reaction is carried out.

The temperature at which the acylation reaction is carried out depends on the reactivity of the starting substrate and that of the acylation agent.

It is between 20° C. and 300° C., preferably between 40° C. and 200° C., and more preferably between 40° C. and 150° C.

The reactants are passed over a catalytic bed comprising at least one zeolite.

The quantity of catalyst used in the process of the invention can vary between wide limits.

The catalyst can represent 0.01% to 50%, preferably 1.0% to 20%, by weight with respect to the aromatic ether or thioether used.

The reaction is generally carried out at atmospheric pressure but lower or higher pressures can also be suitable. Autogenous pressure is used when the temperature of the reaction is more than the boiling point of the reactants and/or products.

The reaction mixture preferably passes through the catalytic bed from bottom to top and is returned from the outlet to the reactant mixing zone to recycle a sufficient number of times to obtain the desired degree of conversion of the substrate, preferably more than 20%, more preferably in the range 50% to 100%. The degree of conversion of the substrate is defined as the ratio between the number of moles of transformed substrate and the number of moles of substrate introduced.

The linear velocity of the liquid stream over the catalytic bed advantageously varies between 0.1 and 10 cm/s, preferably between 0.1 and 5 cm/s.

The residence time for the stream of material on the catalytic bed is between 15 min and 15 hours, for example, preferably between 30 min and 10 hours.

When the reaction is over, a liquid phase comprising the acylated aromatic compound is obtained which can be recovered conventionally, by distillation or recrystallisation from a suitable solvent, after prior elimination of the excess reactants.

The accompanying

Figure 1:
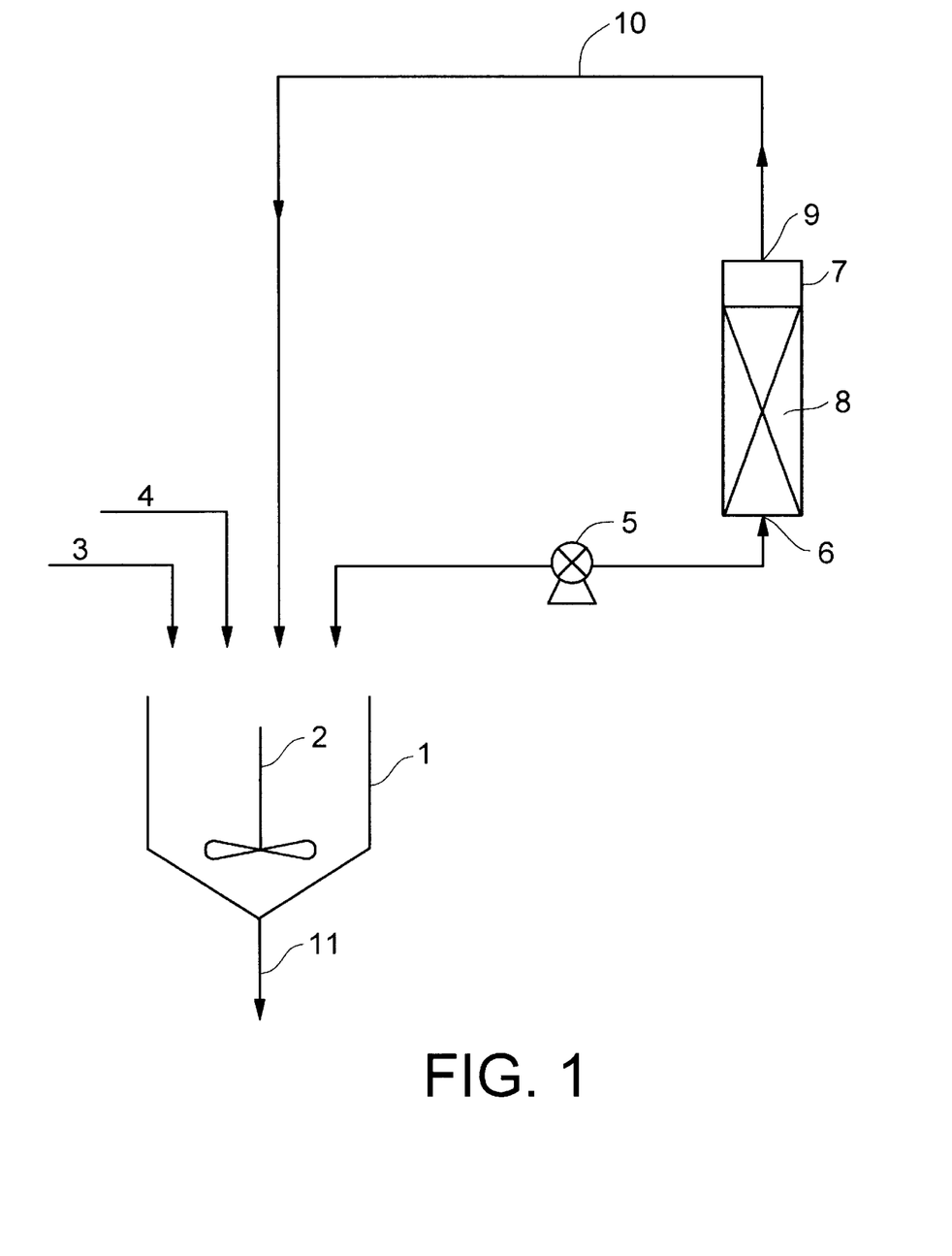
FIG. 1 shows a preferred embodiment of the invention, which is given for better comprehension of the invention.

In a reactor (1), the aromatic compound (preferably an aromatic ether or thioether) and the acylation agent are mixed. The reactor can be stirred or not stirred, provided with inlet valves for the reactants and outlet valves and provided with a heating means or provided with a double envelope for heating the mixture by circulating a liquid at the suitable temperature. Stirring, which is not obligatory, can be carried out using an Impeller® (2).

Aromatic compound (3) and acylation agent (4) are introduced into the reactor (1).

The reaction mixture is sent, using any appropriate means, in particular a centrigal pump (5), to the bottom (6) of a tube reactor (7) comprising the solid zeolitic catalyst disposed in a fixed bed (8).

At the reactor outlet (9), the reaction mixture is sent to reactor (1) via a conduit (10) and thus circulates in a closed loop.

When the reaction is over, the reaction mixture is recovered by emptying mixer (1) via a valve (11) which is not shown in the diagram.

The process of the invention is particularly suitable for preparing 4-methoxyacetophenone, usually known as acetoanisole, by acetylation of anisole.

One advantage of the process of the invention is that the acylation reaction is carried out without O-dealkylation of the starting aromatic ether.

The following examples illustrate the invention without limiting it in any way.

In the examples, the yields quoted are defined as follows:

$$\text{Yield: } RR_{AA} = \frac{\text{number of moles of acylated aromatic compound formed}}{\text{number of moles of acylation agent introduced}} \%$$

EXAMPLES

The operating protocol followed in the different examples is given below. Reference should be made to FIG. 1.

Zeolitic catalyst was charged into a stainless steel reactor (7) to form the catalytic bed which rested on a layer (about 20 mm thick) of glass beads, and the top of the bed was also covered with about 20 mm of glass beads with a diameter of 5 mm.

Anisole was charged at ambient temperature into a 3 liter double envelope Sovirel® reactor; stirring was begun (40 rpm) and it was circulated over the fixed bed for 15 min; the flow rate was maintained at 60 l/h for the whole duration of the reaction. The reaction was observed to be slightly exothermal.

The reaction mixture was heated using a thermostatted bath to produce a constant temperature of 90° C. at the top of the catalytic bed.

When a temperature of 90° C. had been produced in the bed, acetic anhydride was added over 4 hours, keeping the medium circulating.

After addition, the reaction was kept going for 3 hours at 90° C. (i.e., 7 hours in total).

When the reaction was over, the temperature was allowed to fall to 60° C., and the apparatus was emptied. Nitrogen was blown through the fixed bed for 20 minutes.

Example 1

In this example, anisole was acetylated.

A catalyst comprising 40% of binder (alumina) and 60% of a β zeolite sold by PQ was used.

The zeolite used was a zeolite with a Si/Al ratio of 12.5.

It was used in an amount of 21% with respect to the acetic anhydride, i.e., 225 g.

The number of moles of anisole was 20.9 mol and that of the acetic anhydride was 10.45 mol: the anisole/acetic anhydride molar ratio was 2/1.

The reaction temperature was 90° C., as mentioned above.

Gas chromatography showed a yield (RR) of 75% of 4-methoxyacetophenone after 7 hours.

Examples 2 to 5

The above operation was repeated 4 times using the same catalytic bed as above.

The yield for each operation (RR) was respectively 68%, 65%, 62% and 59%.

Example 6

In this example, veratrole was acetylated.

A catalyst comprising 20% of binder (alumina) and 80% of a Y CBV780 zeolite sold by PQ was used.

It was used in an amount of 21% with respect to the acetic anhydride, i.e., 225 g.

The veratrole/acetic anhydride molar ratio was 2/1.

The reaction temperature was 90° C., as mentioned above.

Gas chromatography showed a yield (RR) of 72% of 3,4-dimethoxyacetophenone after 6 hours.

Example 7

In this example, toluene was acetylated, as in Example 1: the difference was that the reactor was larger, namely 20 l.

A catalyst comprising 40% of binder (alumina) and 60% of a β zeolite sold by PQ was used.

The zeolite used was a zeolite with a Si/Al ratio of 12.5.

It was used in an amount of 50% with respect to the acetic anhydride, i.e., 562 g.

The number of moles of toluene was 110 mol and that of the acetic anhydride was 11.00 mol: the toluene/acetic anhydride molar ratio was 10.

The reaction temperature was 150° C., as mentioned above.

Gas chromatography showed a yield (RR) of 63% of 4-methoxyacetophenone after 10 hours.

Example 8

In this example, isobutylbenzene was acetylated.

A catalyst comprising 40% of binder (alumina) and 60% of a β zeolite sold by PQ was used.

The zeolite used was a zeolite with a Si/Al ratio of 12.5.

It was used in an amount of 60% with respect to the acetic anhydride, i.e., 672 g.

The number of moles of isobutylbenzene was 143 mol and that of the acetic anhydride was 11 mol: the isobutylbenzene /acetic anhydride molar ratio was 13.

The reaction temperature was 150° C., as mentioned above.

Gas chromatography showed a yield (RR) of 75% of 4-isobutylacetophenone after 7 hours.

What is claimed is:

1. A process for the acylation of an aromatic compound by reacting said compound with an acylation agent in the presence of a zeolitic catalyst, comprising:

mixing the aromatic compound and the acylation compound thereby forming a reaction mixture;

passing said mixture over a catalytic bed comprising at least one zeolite;

recirculating the reaction mixture from the catalytic bed over the catalytic bed.

2. A process according to claim 1, wherein the aromatic compound has formula (I):

(I)

where:

A represents the residue of a cycle forming all or part of a carbocyclic or heterocyclic, aromatic, monocyclic or polycyclic system; said cyclic residue carries a radical R which represents a hydrogen atom or one or more substituents, which may be identical or different;

n represents the number of substituents in the cycle.

3. A process according to claim 2, wherein the aromatic compound has formula (I) in which residue A, which is optionally substituted, represents the residue:

1° of an aromatic, monocyclic or polycyclic carbocyclic compound,

2° of an aromatic, monocyclic or polycyclic heterocyclic compound,

3° of a compound constituted by linking cycles of an aromatic, monocyclic, polycyclic carbocyclic or heterocyclic compound linked together by:
  a valence bond;
  an alkylene or alkylidene radical containing 1 to 4 carbon atoms;
  one of the following groups:

in these formulae, $R_0$ represents a hydrogen atom or an alkyl radical containing 1 to 4 carbon atoms, or a cyclohexyl or phenyl radical.

4. A process according to claim 2, wherein the aromatic compound has formula (I) in which radical(s) R, which may be identical or different, represent one of the following groups:

a hydrogen atom;

a linear or branched alkyl radical containing 1 to 6 carbon atoms;

a linear or branched alkenyl radical containing 2 to 6 carbon atoms;

a linear or branched alkoxy radical containing 1 to 6 carbon atoms;

a cyclohexyl, phenyl or benzyl radical;

an acyl group containing 2 to 6 carbon atoms;

a radical with formula:
  —$R_1$—OH
  —$R_1$—$COOR_2$
  —$R_1$—CHO
  —$R_1$—$NO_2$
  —$R_1$—CN
  —$R_1$—$N(R_2)_2$
  —$R_1$—CO—$N(R_2)_2$
  —$R_1$—X
  —$R_1$—$CF_3$ in said formulae, $R_1$ represents a valence bond or a divalent, linear or branched, saturated or unsaturated hydrocarbon radical containing 1 to 6 carbon atoms; radicals $R_2$, which may be identical or different, represent a hydrogen atom or a linear or branched alkyl radical containing 1 to 6 carbon atoms; X represents a halogen atom, or fluorine atom;

two radicals R placed on two neighboring carbon atoms may together form with the carbon atoms they carry a cycle containing 5 to 7 atoms.

5. A process according to claim 2, wherein the aromatic compound has formula (I) where n is greater than or equal to 2, two radicals R and the two successive atoms of the aromatic cycle can be bonded together by an alkylene, alkenylene or alkenylidene radical containing 2 to 4 carbon atoms to form a saturated, unsaturated or aromatic heterocycle containing 5 to 7 carbon atoms: one or more carbon atoms can be replaced by a further heteroatom.

6. A process according to claim 1, wherein the aromatic compound has formula (Ia):

(Ia)

where:

A represents the residue of a cycle forming all or part of an aromatic, monocyclic or polycyclic, carbocyclic or heterocycle system: said cyclic residue can carry a radical R representing a hydrogen atom or one or more electron donating substituents, which may be identical or different;

n represents the number of substituents in the cycle.

7. A process according to claim 6, wherein the aromatic compound has formula (Ia) in which:

radical(s) R, which may be identical or different, represent one of the following groups:

a linear or branched alkyl radical containing 1 to 6 carbon atoms;

a linear or branched alkenyl radical containing 2 to 6 carbon atoms, a linear or branched alkoxy radical containing 1 to 6 carbon atoms, a radical with formula:
  —$R_1$—OH
  —$R_1$—$N(R_2)_2$ in said formulae, $R_1$ represents a valence bond or a divalent, linear or branched, saturated or unsaturated hydrocarbon radical containing 1 to 6 carbon atoms, radicals $R_2$, which may be identical or different, represent a hydrogen atom or a linear or branched alkyl radical containing 1 to 6 carbon atoms;

radicals R may be bonded together to form alkylenedioxy or alkylenedithio radicals;

n is a number which is less than or equal to 4.

8. A process according to claim 1, wherein the aromatic compound is an aromatic ether or thioether with formula (I'):

(I')

where:

Y represents an oxygen atom or a sulphur atom;

A represents the residue of a cycle forming all or a portion of an aromatic, monocyclic or polycyclic carbocyclic system comprising at least one group YR': said cyclic residue may carry one or more substituents;

R represents one or more substituents, which may be identical or different;

R' represents a hydrocarbon radical containing 1 to 24 carbon atoms, which can be a linear or branched, saturated or unsaturated acyclic aliphatic radical; a saturated, unsaturated or aromatic, monocyclic or polycyclic cycloaliphatic radical; or a saturated or unsaturated, linear or branched aliphatic radical carrying a cyclic substituent;

R' and R can form a cycle which optionally comprises a further heteroatom;

n is a number which is less than or equal to 4.

9. A process according to claim 8, wherein the aromatic ether or thioether has formula (I') where R' represents:
- a linear or branched, saturated or unsaturated acyclic aliphatic radical containing 1 to 12 carbon atoms; the hydrocarbon chain can optionally be interrupted by a heteroatom, a functional group and/or optionally carry substituents;
- a linear or branched, saturated or unsaturated acyclic aliphatic radical carrying a cyclic substituent which may optionally be substituted: said acyclic radical can be connected to the cycle by a valence bond, a heteroatom or a functional group;
- a saturated carbocyclic radical or a carbocyclic radical comprising 1 or 2 unsaturations in the cycle, and containing 3 to 8 carbon atoms; said cycle is optionally substituted;
- an aromatic carbocyclic radical containing at least 4 carbon atoms.

10. A process according to claim 8, wherein the aromatic ether or thioether has formula (I') in which R' represents a linear or branched allyl radical containing 1 to 6 carbon atoms.

11. A process according to claim 8, wherein the aromatic ether or thioether has formula (I') in which residue A represents the residue of an aromatic monocyclic carbocyclic compound containing at least 4 carbon atoms, or the residue of a polycyclic carbocyclic compound, residue: A can carry one or more substituents on the aromatic ring.

12. A process according to claim 8, wherein the aromatic ether or thioether has formula (I'a):

(I'a)

where:
- n is a number which is less than or equal to 4;
- Y represents an oxygen atom or a sulphur atom;
- radical R' represents a linear or branched alkyl radical containing 1 to 6 carbon atoms;
- radical(s) R, which may be identical or different, represent one of the following atoms or groups:
  - a hydrogen atom
  - a linear or branched alkyl radical containing 1 to 6 carbon atoms
  - a linear or branched alkenyl radical containing 2 to 6 carbon atoms
  - a cyclohexyl, phenyl or benzyl radical
  - a linear or branched alkoxy radical containing 1 to 6 carbon atoms
  - an acyl group containing 2 to 6 carbon atoms;
  - a radical with formula:
    - —$R_1$—OH
    - —$R_1$—$COOR_2$
    - —$R_1$—CHO
    - —$R_1$—$NO_2$
    - —$R_1$—CN
    - —$R_1$—$N(R_2)_2$
    - —$R_1$—CO—$N(R_2)_2$
    - —$R_1$—X
    - —$R_1$—$CF_3$ in said formulae, $R_1$ represents a valence bond or a divalent, linear or branched, saturated or unsaturated hydrocarbon radical containing 1 to 6 carbon atoms; radicals $R_2$, which may be identical or different, represent a hydrogen atom or a linear or branched alkyl radical containing 1 to 6 carbon atoms; X represents a halogen atom;
- radicals R and R' placed on two neighbouring carbon atoms may together form with the carbon atoms they carry a cycle containing 5 to 7 atoms, optionally comprising a further heteroatom.

13. A process according to claim 12, wherein the aromatic ether or thioether has formula (I'a) where when n is greater than or equal to 1, radicals R' and R and the two successive atoms of the benzenic cycle can be bonded together to form an alkylene, alkenylene or alkenylidene radical containing 2 to 4 carbon atoms to form a saturated, unsaturated or aromatic heterocycle containing 5 to 7 atoms in which one or more carbon atoms can be replaced by a further heteroatom: radicals YR' and R form a methylenedioxy, ethylenedioxy, methylenedithio or ethylenedithio radical.

14. A process according to claim 8, wherein the aromatic ether or thioether has formula (I') or (I'a) in which:
- n equals 0 or 1;
- R' represents a linear or branched alkyl radical containing 1 to 6 carbon atoms or a phenyl radical;
- R represents a linear or branched alkyl radical containing 1 to 6 carbon atoms, or a linear or branched alkoxy radical containing 1 to 4 carbon atoms;
- radicals YR' and R form a methylenedioxy, ethylenedioxy, methylenedithio or ethylenedithio radical.

15. A process according to claim 1, wherein the aromatic compound is benzene, toluene, isobutylbenzene, anisole, phenetole, veratrole, 1,2-methylenedioxybenzene, 2-methoxynaphthalene or thioanisole.

16. A process according to claim 1, wherein the acylation agent comprises carboxylic acids and their halide or anhydride derivatives.

17. A process according to claim 16, wherein the acylation agent has formula (II):

(II)

where:
- $R_3$ represents:
  - a linear or branched, saturated or unsaturated aliphatic radical containing 1 to 24 carbon atoms; a monocyclic or polycyclic saturated, unsaturated or aromatic cycloaliphatic radical containing 3 to 8 carbon atoms; or a linear or branched, saturated or unsaturated aliphatic radical carrying a cyclic substituent;
- X' represents:
  - a halogen atom;
  - a hydroxyl group;
  - a —O—CO—$R_4$ radical, where $R_4$, which may be identical to or different from $R_3$, has the same meaning as $R_3$: $R_3$ and $R_4$ may together form a divalent linear or branched, saturated or unsaturated aliphatic radical containing at least 2 carbon atoms.

18. A process according to claim 17, wherein the acylation agent has formula (II) in which X' represents a chlorine atom and $R_3$ represents a linear or branched alkyl radical containing 1 to 12 carbon atoms, the hydrocarbon chain can optionally be interrupted by a heteroatom or by a functional group or it carries substituents, $R_3$ also representing a phenyl radical; X' represents a —O— CO—$R_4$ radical, in which $R_3$ and $R_4$ are identical and represent an alkyl radical containing 1 to 4 carbon atoms, and optionally carry halogen atoms or a phenyl radical.

19. A process according to claim 17, wherein the acylation agent is selected from:
a acetic anhydride;
propanoic anhydride
butyric anhydride;
isobutyric anhydride;
trifluoroacetic anhydride;
benzoic anhydride;
monochloroacetyl anhydride;
dichloroacetyl anhydride;
acetyl chloride;
monochloroacetyl chloride;
dichloroacetyl chloride;
propanoyl chloride;
isobutanoyl chloride;
pivaloyl chloride;
stearoyl chloride;
crotonyl chloride;
benzoyl chloride;
chlorobenzoyl chlorides;
p-nitrobenzoyl chloride;
methoxybenzoyl chlorides;
naphthoyl chlorides;
acetic acid;
benzoic acid.

20. A process according to claim 16, wherein the acylation agent is acetic, propanoic, benzoic, monochloroacetyl, or dichloroacetyl anhydride, or benzoyl chloride.

21. A process according to claim 1, wherein the catalyst is a natural or synthetic zeolite.

22. A process according to claim 21, wherein the zeolite is a natural zeolite selected from: chabazite, clinoptilolite, erionite, mordenite, phillipsite, and offretite.

23. A process according to claim 22, wherein the zeolite is a synthetic zeolite comprising:
zeolites with a one-dimensional network comprising ZSM-4 zeolite, L zeolite, ZSM-12 zeolite, ZSM-22 zeolite, ZSM-23 zeolite, or ZSM-48 zeolite;
zeolites with a two-dimensional network comprising β zeolite, mordenite, or ferrierite;
zeolites with a three-dimensional network comprising Y zeolite, X zeolite, ZSM-5 zeolite, ZSM-11 zeolite, or offretite;
mesoporous MCM type zeolite.

24. A process according to claim 23, wherein the zeolite is a β and a Y zeolite.

25. A process according to claim 21, wherein the zeolite is used alone or mixed with an inorganic matrix.

26. A process according to claim 1, wherein the ratio between the number of moles of aromatic compound and the number of moles of acylation agent is between 0.1 and 20.

27. A process according to claim 1, wherein the ratio between the number of moles of aromatic compound and the number of moles of acylation agent is at least 1.

28. A process according to claim 1, wherein the quantity of catalyst is 0.01% to 50%, by weight with respect to the aromatic compound used.

29. A process according to claim 1, wherein the temperature at which the acylation reaction is carried out is in the range 20° C. to 300° C.

30. A process according to claim 1, wherein the reaction is carried out at atmospheric pressure.

31. A process according to claim 1, wherein the reaction mixture passes through the catalytic bed from bottom to top and at the outlet.

32. A process according to claim 31, wherein the degree of conversion is more than 20%.

33. A process according to claim 1, wherein the linear velocity of the liquid stream over the catalytic bed is between 0.1 and 10 cm/s.

34. A process according to claim 1, wherein the residence time of the material stream on the catalytic bed is between 15 minutes and 15 hours.

35. A process according to claim 1, wherein when the reaction is over, a liquid phase comprising the acylated aromatic compound is recovered.

* * * * *